United States Patent [19]

Kugler et al.

[11] Patent Number: 5,427,723

[45] Date of Patent: Jun. 27, 1995

[54] INTERMITTENT, MACHINE-DIRECTION FLUFF CONTOURING METHOD

[76] Inventors: Joseph M. Kugler, N1453 Wildwood Dr., Greenville, Wis. 54942; Peter J. Krautkramer, 2637 S. Jackson St., Appleton, Wis. 54915; Lyle T. Lamers, 2201 Berry Dr.; Douglas P. Rammer, N333 Rogers La., both of Appleton, Wis. 54915

[21] Appl. No.: 148,056

[22] Filed: Nov. 3, 1993

Related U.S. Application Data

[62] Division of Ser. No. 955,587, Oct. 2, 1992, Pat. No. 5,288,220.

[51] Int. Cl.$^6$ .................... B29D 7/00; D04H 1/70
[52] U.S. Cl. .................... 264/119; 19/301; 26/16; 26/30; 162/120; 264/160; 264/167; 425/83.1; 425/299; 425/362
[58] Field of Search ............ 28/109, 111; 26/16, 26/30; 19/300, 301; 425/80.1, 81.1, 82.1, 83.1, 294, 328, 373, 374; 264/293, 284, 112, 119, 139, 167, 160, 162; 162/109, 116, 117, 120

[56] References Cited

U.S. PATENT DOCUMENTS

| | | | |
|---|---|---|---|
| 1,294,516 | 2/1919 | Moore | 26/16 |
| 2,847,086 | 8/1958 | Muller | 264/112 |
| 3,184,367 | 5/1965 | White | 26/30 |
| 3,328,505 | 6/1967 | Spencer | 264/284 |
| 3,961,012 | 6/1976 | DiMaio | 264/112 |
| 3,969,565 | 7/1976 | Forrest | 264/284 |
| 4,005,957 | 2/1977 | Savich | 425/80.1 |
| 4,016,628 | 4/1977 | Kolbach | 425/82.1 |
| 4,135,024 | 1/1979 | Callahan et al. | 162/117 |
| 4,507,173 | 3/1985 | Klowak et al. | 162/113 |
| 4,619,723 | 10/1986 | Takagi | 264/119 |
| 4,626,184 | 12/1986 | Hammond | 264/167 |
| 4,636,159 | 1/1987 | Heller et al. | 425/80.1 |
| 4,666,647 | 5/1987 | Enloe et al. | 264/121 |
| 4,690,853 | 9/1987 | Hammond | 428/157 |
| 4,761,258 | 8/1988 | Enloe | 264/518 |
| 4,892,470 | 1/1990 | Farrington et al. | 425/80.1 |
| 4,927,582 | 5/1990 | Bryson | 264/113 |

FOREIGN PATENT DOCUMENTS

| | | | |
|---|---|---|---|
| 2371291 | 7/1978 | France | 425/425 |

*Primary Examiner*—Jay H. Woo
*Assistant Examiner*—Duane S. Smith
*Attorney, Agent, or Firm*—Paul Yee

[57] ABSTRACT

A distinctive method for contouring a fibrous web includes the steps of (a) providing a fibrous web which defines an interconnected series of appointed article segments along a length dimension of said web, and (b) conveying said web at a selected speed along an appointed machine direction. The method also includes the step of (c) removing predetermined quantities of fibers from selected regions of said fibrous web with a moving, outer peripheral scarfing surface, which is movable along a selected movement direction. The scarfing surface is constructed to provide each of the article segments with a selected contoured basis weight which varies along the length dimension of said segment in a selected correspondence with a predetermined scarfing pattern. The scarfing pattern is provided by the outer peripheral scarfing surface and is variably patterned along the movement direction of the scarfing surface. A relative movement between the conveying step (b) and the removing step (c) is regulated to provide the selected correspondence and to thereby form said selected contoured basis weight on substantially each of the appointed article segments.

20 Claims, 9 Drawing Sheets

INTERMITTENT, MACHINE-DIRECTION FLUFF CONTOURING METHOD

This is a divisional application of application Ser. No. 07/955,587, filed on Oct. 2, 1992, now U.S. Pat. No. 5,288,220.

FIELD OF THE INVENTION

The present invention relates to a method and apparatus for contouring the surface of a fibrous web of material. More particularly, the present invention relates to a method and apparatus for contouring the thickness and/or basis weight distribution of airlaid, fibrous web material along the length dimension of the web.

BACKGROUND OF THE INVENTION

Conventional techniques for forming airlaid webs of fibrous material have employed drum formers with contoured forming screens located on the surface of the drum. For example, see U.S. Pat. No. 4,666,647 issued May 19, 1987 to Enloe et al. and U.S. Pat. No. 4,761,258 issued Aug. 2, 1988 to Enloe. Conventional techniques have also formed airlaid fibrous webs on a belt-type forming screen. For example, see U.S. Pat. No. 4,927,582 issued May 22, 1990 to Bryson.

It has been desirable to produce three-dimensional, contoured shapes in the fibrous webs formed on the surface of an endless-belt-type of forming screen. It has, however, been difficult to reliably form such shapes on a belt-type of forming system. If the forming belt is constructed with three-dimensional contour shapes formed therein, the shaped contours inhibit the movement of the endless belt screen around the turn rolls positioned at the ends of the apparatus. If the contoured shapes are molded within a relatively thick, forming screen belt, it has been difficult to reliably articulate the thick belt structure to allow high speed movement around the turn rolls positioned at the ends of the belt.

To form the desired three-dimensional shapes, conventional systems have also incorporated scarfing rolls having a peripheral scarfing surface which is contoured along the axial, length dimension of the scarfing rolls. Such scarfing rolls have been able to contour the basis weight distribution along the cross-direction of the fibrous web.

To contour the shape and basis weight distribution along the longitudinal, machine-direction of the web, some conventional techniques have incorporated an eccentrically-shaped displacement roller to selectively move the belt-type forming screen and reposition the fibrous web to thereby generate three-dimensional contours and a variable basis weight distribution along the machine-direction of the fibrous web. For example, see U.S. Pat. No. 4,690,853 issued Sep. 1, 1987, to P. Hammond.

Conventional techniques, such as those described above, have not adequately generated desired machine-direction contours and basis weight distributions along the lengthwise dimension of a fibrous web. Techniques which deform or deflect the forming screen can place additional, undesired stresses on the forming screen. The techniques may also be speed limited since inertia can prevent the screen from accurately following the contours of the deflecting roll. Other techniques, which intermittently displace a vertical positioning of the scarfing roll, may also be speed limited due to the inertia of the scarfing roll mechanism. Such conventional techniques have also been less able to form relatively abrupt changes in the basis weight distribution along the machine direction. As a result, there has been a continued need for an improved technique for selectively varying the basis weight distribution along the lengthwise, machine-direction of a fribrous web, such as a fibrous web composed of airlaid wood pulp fluff.

BRIEF DESCRIPTION OF THE INVENTION

An apparatus aspect of the present invention provides a distinctive apparatus for contouring a fibrous web. The apparatus comprises supplying means for providing a fibrous web which defines an interconnected series of appointed article segments along a length dimension of the web. A conveying means moves the web at a selected speed along an appointed machine direction, and a scarfing means removes predetermined quantities of fibers from selected regions of the fibrous web. The scarfing means is constructed to provide each of the article segments with a selected contoured basis weight which varies at least along the length dimension of the segment in a selected correspondence with a predetermined scarfing pattern. The scarfing pattern is provided by an outer peripheral surface of the scarfing means, and the pattern is configured to have a selected variation at least along a movement direction of the scarfing means. A regulating means controls a relative movement between the conveying means and the scarfing means to provide the selected correspondence and to thereby form the selected contoured basis weight on substantially each of the article segments.

A process aspect of the invention provides a distinctive method for contouring a fibrous web. The method comprises the step of providing a fibrous web which defines an interconnected series of appointed article segments along a length dimension of the web. The web is conveyed at a selected speed along an appointed machine direction, and predetermined quantities of fibers are removed from selected regions of the fibrous web with a scarfing means. The scarfing means is constructed to provide each of the article segments with a selected contoured basis weight which varies along the length dimension of the segment in a selected correspondence with a predetermined scarfing pattern which is provided by an outer peripheral surface of the scarfing means and is variably patterned along a movement direction of the scarfing means. A relative movement between the conveying step and the removing step is regulated to provide the selected correspondence and to thereby form the selected contoured basis weight on substantially each of the appointed article segments.

The present invention can more efficiently form desired thickness contours and basis weight variations along the machine direction of a fibrous web, such as a fibrous web composed of airlaid wood pulp fibers. Particular aspects of the invention can more readily adjust and control the desired thickness contours and basis weight distributions. In addition, the technique of the invention can be more readily adaptable to a high speed manufacturing operation.

BRIEF DESCRIPTION OF THE DRAWINGS

The present invention will be more readily understood and further advantages will become apparent when reference is made to the following detailed description of the invention and the drawings, in which.

DETAILED DESCRIPTION OF THE INVENTION

Fibrous webs, such as webs composed of wood pulp fluff, have been employed to construct absorbent articles such as disposable diapers, feminine care products, incontinence garments and the like. While the present invention is described in the context of a fibrous web composed of airlaid wood pulp fluff, it should be readily apparent that the invention may also be employed to contour the thickness of other types of fibrous webs. Such webs may include, for example, bonded carded webs, spunbonded webs, meltblown webs, coform webs and combinations thereof. The webs may be composed of natural fibers, synthetic fibers, superabsorbent particles or combinations and blends thereof.

Figure 1:
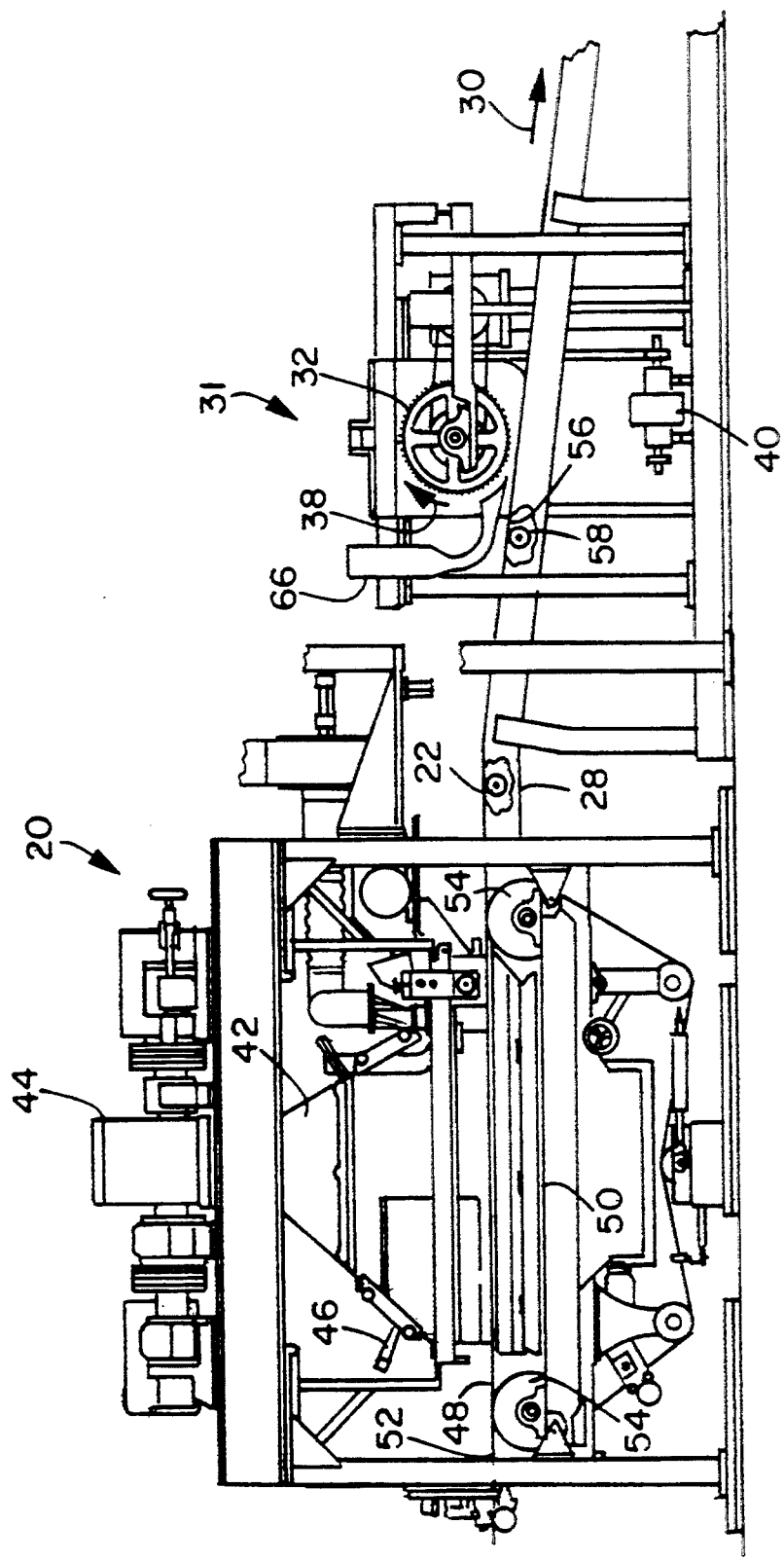
FIG. 1 representatively shows a side elevational view of the apparatus of the invention.
Figure 5:
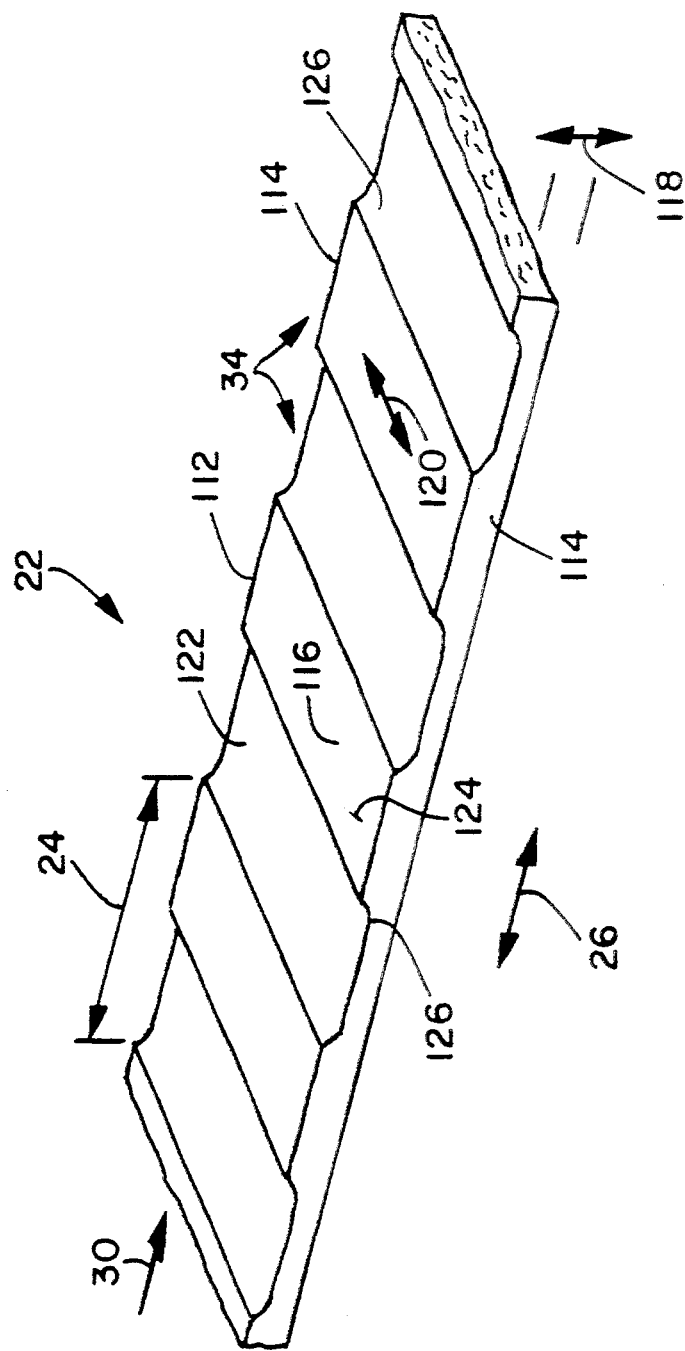
FIG. 5 shows a representative fibrous web which includes a thickness contour and a predetermined basis weight variation along the machine direction of the fibrous web.

With reference to FIG. 1, an apparatus for contouring a fibrous web includes a supplying means, such as fiberizer 20, for providing a fibrous web 22 which defines an interconnected series of appointed article segments 24 (FIG. 5) distributed along a length dimension 26 of the fibrous web. A conveying means, such as conveyor 28, moves the web at a selected speed along an appointed machine direction 30, and a scarfing means, such as a mechanism including scarfing roll 32, removes predetermined quantities of fibers from selected regions of fibrous web 22. The scarfing means is constructed to provide each of the article segments 24 with a selected, contoured basis weight which varies at least along a length dimension 26 of segment 24 in a selected correspondence with a predetermined scarfing pattern 34 (FIG. 5). The scarfing pattern is provided by an outer peripheral surface 36 (FIG. 3) of the scarfing means, and the pattern is configured to have a selected variation at least along a movement direction 38 of the scarfing means. Regulating means, such as a mechanism including phasing transmission 40, controls a relative movement between the conveying means and the scarfing means to provide the selected correspondence therebetween and to thereby form the selected contoured basis weight on substantially each of article segments 24. Further aspects of the invention are set forth in the present specification.

Fiberizer 20 includes a fluff forming chamber 42 which guides and contains the fibers employed to form fibrous web 22. Hammermill 44 is connected to chamber 42 to disintegrate a supply of cellulose sheet material into a plurality individual fibers. If desired, a supply nozzle 46 may be employed to direct particles of superabsorbent material into forming chamber 42. Suitable devices for forming airlaid fibrous webs containing superabsorbent materials therein are described in U.S. Pat. Nos. 4,927,582 issued May 22, 1990 to R. Bryson (Attorney Docket No. 7637) and 5,028,224 issued Jul. 2, 1991 to C. Pieper et al. (Attorney Docket No. 8761), the disclosures of which are hereby incorporated by reference to the extent that they are consistent herewith. A conventional forming screen 48 travels through chamber 42 and, in the shown embodiment, is configured in the form of an endless belt which is suitably driven to travel about turn rollers 54. In particular embodiments, a lager of forming tissue 52 can be directed into chamber 42 and transported on top of forming screen 48 to receive a deposit of airlaid fibers thereon. A vacuum box 50 is located beneath forming screen 48, and a low pressure area induced within the vacuum box operably draws an airflow through forming tissue 52, and through forming screen 48. The airflow operably carries and deposits the wood pulp fibers onto forming tissue 52. The speed of forming screen through chamber 42 and the airflows generated within the forming chamber are adjusted in a conventional manner to control the amount of fibers deposited on forming tissue 52. Accordingly, the fibrous web 22 leaving forming chamber 42 has a selected basis weight and thickness dimension 118 (FIG. 5).

The shown embodiment of fibrous web 22 has a basis weight within the range of about 139–800 gsm and a density within the range of about 0.02–0.03 grams/cc. As a result, the fibrous web has a thickness within the range of about 0.6–2.9 centimeters. The basis weight and thickness dimension, however, can be uneven because of localized variations in the air flow through chamber 42.

Fibrous web 22 is directed onto a conveyor 28 composed of conveyor belt 56 and conveyor rollers 58. Conveyor 28 transports fibrous web 22 at a selected speed to a scarfing means which removes selected amounts of fibrous material from web 22 to generate a web having a predetermined distribution of basis weights and thickness dimensions along the surface extent thereof. To provide a more uniform thickness dimension, for example, conventional techniques have employed a scarfing roll which abrades and substantially levels the surface of fibrous web 22 to remove the various hill s and valleys from the deposited fibrous material and provide a more uniform thickness across the surface of the web.

Conventional scarfing rolls have also been constructed with contoured outer surfaces wherein the diameter of the scarfing roll varies with respect to the position along the axial length of the roll. Such profiled scarfing rolls are capable of contouring the basis weight of fibrous web 22 along the cross deckle direction 120 (FIG. 5) of the web. Conventional scarfing rolls, however, have not been able to adequately contour fibrous web 22 along the length dimension 26 of the web.

Figure 2:
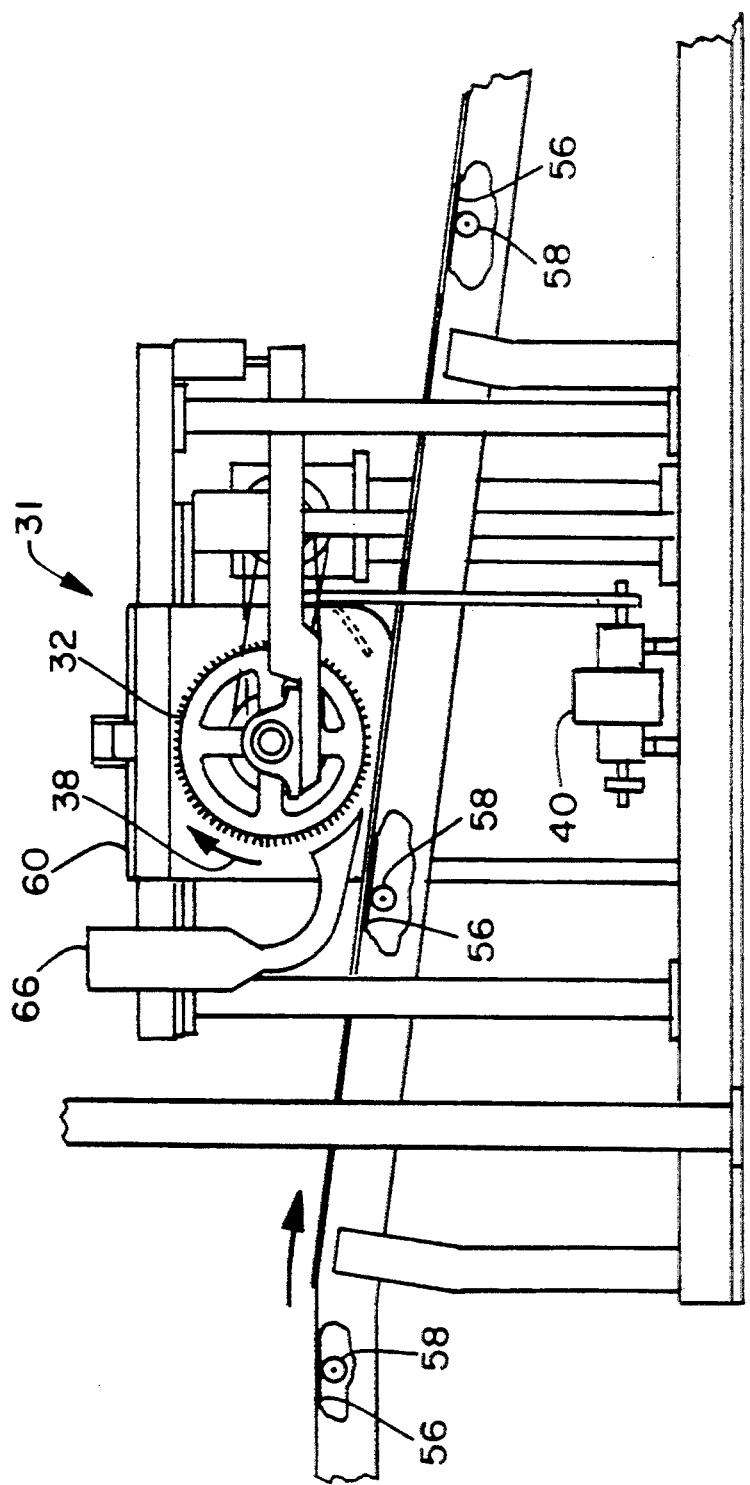
FIG. 2 representatively shows an side elevational view of a scarfing module employed with the invention.
Figure 3:
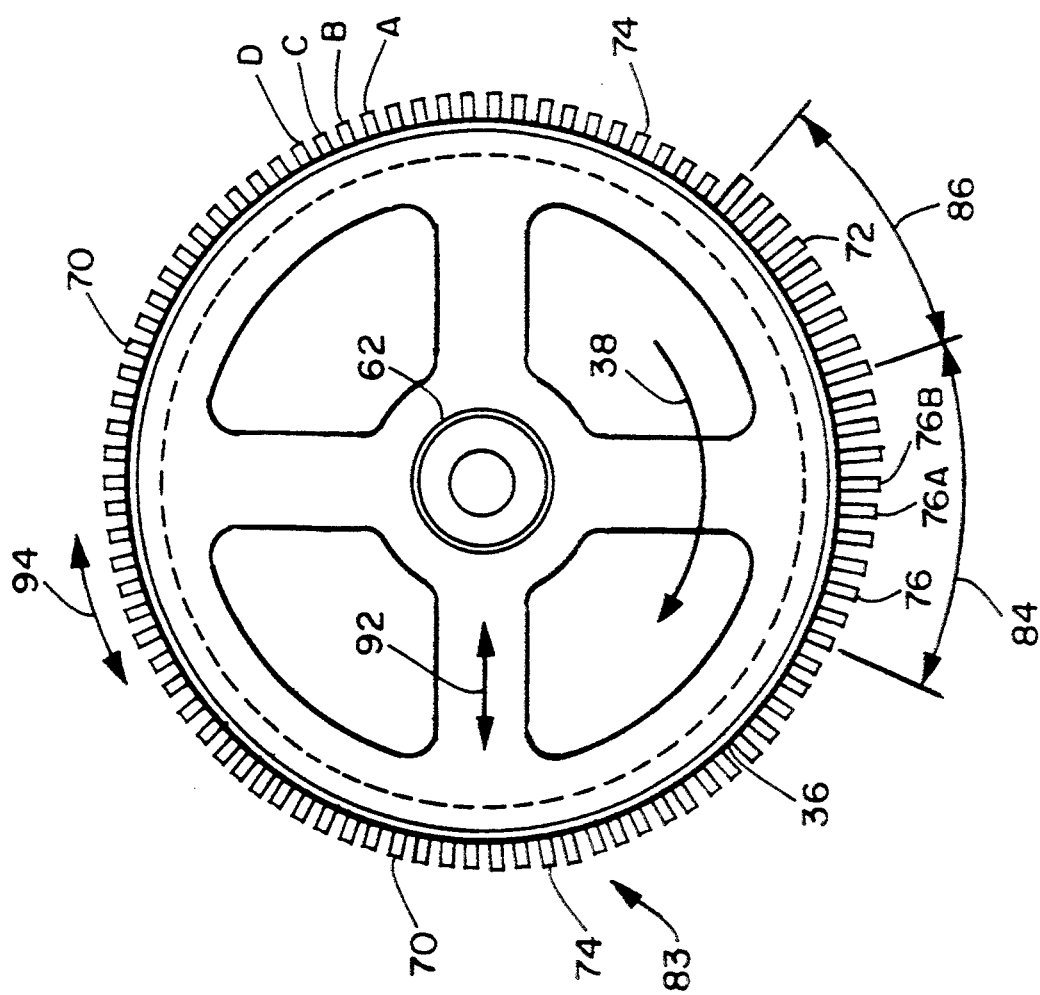
FIG. 3 shows a side elevational view of a representative scarfing roll employed with the invention.

To provide an improved capability of varying and contouring the basis weight of fibrous web 22 along length dimension 26 of the web, the present invention employs scarfing means having a distinctive timed scarfing roll 32. With reference to FIGS. 2 and 3, the illustrated embodiment representatively shows scarfing module 31 having a timed scarfing roll 32, which is located in housing 60 and rotates about rotational axis 62 along a rotational direction 38. Axis 62 is preferably aligned substantially parallel to a major, facing surface of web 22, and substantially perpendicular to machine direction 30. The scarfing roll includes a mechanism which abrades the surface of web 22 or otherwise removes fibrous material from the web surface in accordance with a predetermined pattern. Accordingly, the web thickness dimension 118 is smaller at certain locations and relatively larger at other locations. Where web 22 is more abraded by scarfing roll 32, the web has a relatively lower basis weight and/or thickness, and where web 22 is less abraded by scarfing roll 32, the web has a relatively higher basis weight and/or thickness. Fibrous material removed from web 22 is, in turn, removed from housing 60 by a suitable vacuum mechanism that draws the loose fibrous material through take-away duct 66.

With reference to FIGS. 2 and 3, scarfing module 31 includes a timed scarfing roll 32 which has an axial length dimension 90 (FIG. 7), a circumferential dimension 94 and a radial dimension 92. The roll is preferably cylindrical in shape, but could optionally be non-cylindrical. The illustrated embodiment includes a rotatable, substantially cylindrical, scarfing roll 32 which has a rotational axis 62 and an outer peripheral surface 36. The peripheral surface extends across an length dimension 90 and a circumferential dimension 94 of the roll. With respect to its peripheral surface 36, the shown embodiment of the scarfing roll has a body diameter of about 16 in (about 40.6 cm) and an axial length of up to about 14 in (about 35.6 cm).

A selected scarfing pattern 34 is provided on the outer peripheral surface of scarfing roll 32. In the shown embodiment, the scarfing pattern is provided by a system of scarfing pins 70 connected to the outer surface of the scarfing roll. The pins extend substantially along a radial dimension of the scarfing roll, and the lengths of the individual pins are varied in accordance with a predetermined pattern. The pattern is constructed and arranged to produce a generally corresponding basis weight and/or thickness contour which is patterned across the surface of web 22. More particularly, the invention provides for a distinctively patterned sequence of contact between scarfing pins 70 and moving web 22. The moving pins carried by scarfing roll 32 pick away selected quantities of fibers from predetermined regions of the web, and the windage created by the moving pins helps to move the loose fibers from housing 60 through duct 66.

The shown plurality of individual scarfing pins 70 are distributed across outer Surface 36, and the lengths of the pins are arranged to extend at least partially along a radial direction 92 of the roll. Preferably, the pins extend substantially perpendicular to surface 36. Pins 70 are constructed with a plurality of lengths and are selectively located to provide for the desired scarfing pattern. In the shown embodiment, for example, the maximum pin length is about 1 in (about 2.54 cm). As a result, the scarfing roll provides for a maximum scarf diameter of about 18 in (about 45.7 cm), as measured with respect to the free-end tips of pins 70. Where the scarfing roll has the form of a right, circular cylinder which rotates about a central axis, the lengths of the individual pins 70 can be effectively represented by the distance between peripheral surface 36 and the unconnected, distal end of the individual pin. In a more general sense, however, the effective length of an individual pin is determined by the distance between the rotational axis of the scarfing roll and the distal free end of the individual scarfing pin. This more general determination of the pin length would be important if the scarfing roll had a non-cylindrical shape or had an eccentric axis of rotation. Pins 70 are attached to the surface of scarfing roll 32 with suitable fastening means, such as welding or the like. Preferably, pins 70 are removably attached to the outer surface of scarfing roll 32 with releasable fastening means, such as screws, clamps, or the like. When employing releasable pins, individual pins can be selectively removed, and then replaced with other pins having different pin lengths. Accordingly, the distribution pattern of pin lengths can be adjusted to selectively change and modify the predetermined pin pattern positioned across the outer surface of scarfing roll 32. In the shown embodiment, pins 70 are arranged in a system of substantially linear rows, which extend along the axial dimension 90 of scarfing roll 32. The adjacent pin rows are staggered with respect to each other, and the stagger pattern repeats every four rows of pins. The shown embodiment, within each set of four rows, the individual rows are designated A, B, C, and D. When the pins in adjacent rows are compared, the pins are offset from each other by a discrete distance along the axial dimension of the scarfing roll to provide the staggered configuration. Within a particular row of pins, the pin spacing along axial direction 90 is within the range of about 0.3–2.2 centimeters. Alternatively, the axial direction pin spacing is within the range of about 0.64–1.9 centimeters, and optionally is within the range of about 0.9–1.6 centimeters to provide desired performance levels.

In a particular aspect of the invention, the spacing between individual rows of pins, as measured along the circumference of scarfing roll 32, is selected to cooperate with the pattern of pin lengths to help generate relatively abrupt changes in the basis weight and thickness of fibrous web 22 along machine direction 30 of the web. In particular, the pin row spacing can be within the range of about 0.3–2.9 centimeters, Preferably, the pin row spacing is within the range of about 0.6–2.2 centimeters, and more preferably is within the range of about 0.9–1.6 centimeters to better provide desired operability.

In another aspect of the invention, the pin row spacing along the circumference of scarfing roll 32 is configured in an arrangement wherein the arc length distance between adjacent pin rows is within the range of about 0.90–8.0 degrees of arc. Preferably, the arc distance is within the range of about 1.7–6.3 degrees of arc, and more preferably is within the range of about 2.7–4.5 degrees of arc.

A predetermined scarfing pattern 34 can be provided by configuring a plurality of individual pins 70 with different lengths, and selectively locating the different length pins at selected locations along outer surface 36 of scarfing roll 32 in accordance with a predetermined pattern. Long pins 72 with relatively greater lengths are grouped and positioned at first regions 86 of surface 36 which are appointed to correspond to relatively low basis weight regions of an article segment 24. Short pins 74 are configured with relatively smaller lengths, and are grouped and placed at second regions 88 of outer surface 36 which are appointed to correspond to relatively high basis weight regions of the article segment. In addition, intermediate length pins 76 can be positioned in a graduated arrangement of decreasing pin lengths at third, transition regions 84 of outer surface 36 which are appointed to correspond to basis weight transition zones in the article segment.

With reference to intermediate length pins 76, the change in pin length per degree of arc length along circumferential direction 94 is not more than about 0.09 centimeters per degree, preferably is not more than about 0.05 centimeters per degree and more preferably is not more than about 0.03 centimeters per degree to provide desired performance characteristics. In other aspects of the invention, the change in pin length per degree of arc length is not less than about 0.009 centimeters per degree. Preferably, such change in pin length is not less than about 0.012 centimeters per degree, and more preferably, is not less than about 0.02 centimeters per degree to provide selected performance.

The intermediate length pins 76 are located in at least one transition region 84 which extends at least along the circumferential dimension 94 of scarfing roll 32. The transition region has a distribution of pins in which the lengths of individual pins 74 are selected to provide a gradual change of pin length along the circumferential direction through the transition region. The transition region generally corresponds to a basis weight transition zone 126 (FIG. 5) on article segment 24 wherein the basis weight transitions between a high basis weight region and a relatively lower basis weight region. The present invention can advantageously produce a basis weight transition zone wherein the length of the transition zone on article segment 24 is less than the radius of scarfing roll 32. In particular arrangements, the length of the transition zone on article segment 24 is not more than about 30% of the radius of the scarfing roll, and optionally, is not more than about 25% of the radius of the scarfing roll.

Figure 4:
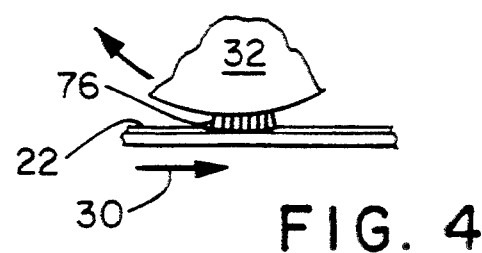
FIG. 4 representatively shows the operation of the transition zone on a scarfing roll wherein a distribution of scarfing pins are configured with gradually increasing pin lengths.
Figure 4A:
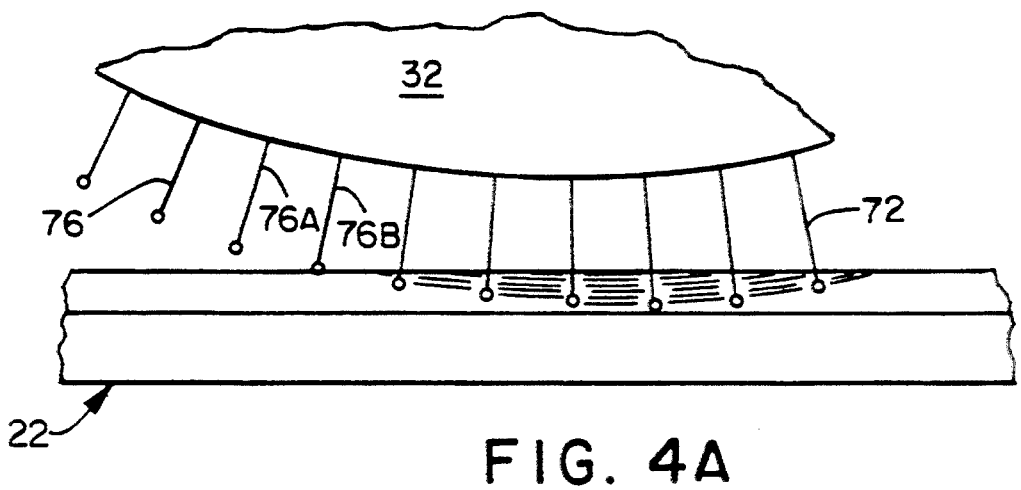
FIG. 4A representatively shows an enlarged view of FIG. 4.
Figure 4B:
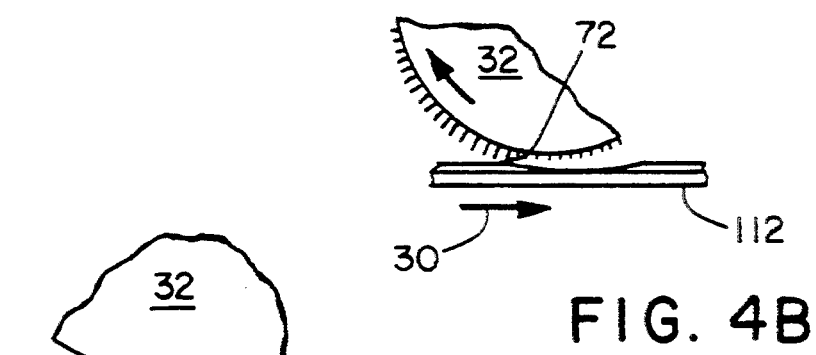
FIG. 4B representatively shows the operation of scarfing pins employed to form a relatively low basis weight region of a contoured fibrous web.
Figure 4C:
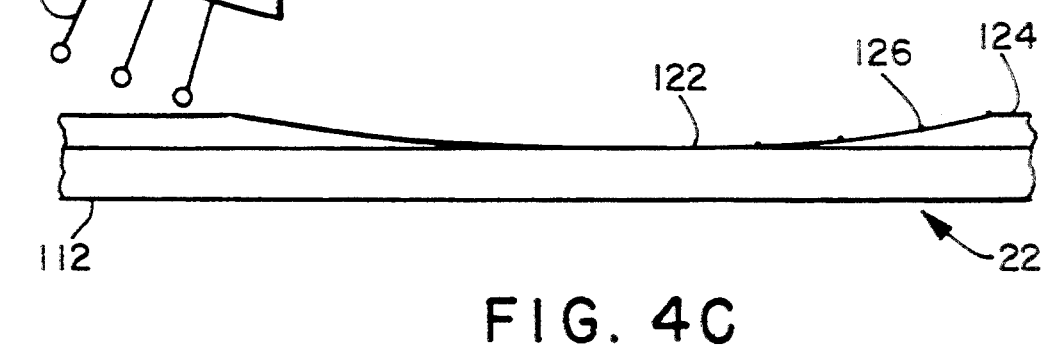
FIG. 4C representatively shows an enlarged view of FIG. 4B.

With reference to FIG. 4, a representative transition region 84 of scarfing roll 32 begins with at least one row of pins 76A which have a length slightly longer than short pins 74. These pins cut a slightly deeper path into the moving fibrous web 22 and initiate the formation of web transition zone 126. A successively following grouping of one or more pin rows is composed of pins 76B which have a slightly longer length than pins 76A. Accordingly, these pins cut further into the thickness of web 22 and continue the formation of web transition zone 126. Similarly, additional sequences of rows of gradually longer pins 76C, 76D, etc. can be employed to gradually cut deeper into moving web 22 until the desired, maximum depth of cut is obtained. In a particular embodiment of the invention, the transition region can include approximately 9 rows of intermediate length pins that gradually increase in length at each successive pin row. Once the maximum depth of cut is generated along an appointed-length-wise section of web 22, the pin length of the succeeding pin rows may be immediately returned to the length of short pins 74. Optionally, the pin length may be gradually increased back to the length of the short pins, as desired.

In particular aspects of the invention, pins 70 are arranged to form a desired scarfing pattern 34 which is configured as a periodically repeating pattern. In particular, the scarfing pattern can be a periodically repeating pattern which repeats a whole-integer number of times along the circumference of scarfing roll 32. Examples of such whole-number integers include 1, 2, 3, etc.. The whole-number integer substantially corresponds to a number of article segments 24 appointed for movement past scarfing roll 32 per each revolution of the scarfing roll.

For example, the shown embodiment of scarfing roll 32 has a single scarfing pattern distributed along the circumference of the scarfing roll, and the scarfing roll turns one revolution each time one article segment moves past the location of the scarfing roll. In particular aspects of the invention, the desired scarfing pattern may be repeated a plurality of times along the circumference of the scarfing roll, wherein the plurality is defined by a whole-number integer. For a particular whole-number of repeated patterns, the invention is configured to move that whole-number of article segments past the location of the scarfing operation of scarfing roll 32 during each revolution of the scarfing roll. For example, where the scarfing pattern is repeated twice along the circumference of scarfing roll 32, two article segments will be transported past the scarfing roll per each revolution turned by the scarfing roll. Similarly, where the scarfing pattern is repeated three times along the circumference of scarfing roll 32, three article segments will be moved through the scarfing operation during each revolution of the scarfing roll.

The location and shape of the basis weight contour along each article length segment 24 can be controlled by regulating the speed of web 22 along machine direction 30, and regulating the rotational speed and direction of the scarfing roll. In the shown embodiment, conveyor 28 moves web 22 at a substantially constant speed. Scarfing roll 32 turns with a selected, substantially constant rotational velocity which cooperates with the speed imparted to web 22 by conveyor 28 to provide an operable impact speed between the moving fibrous web and the scarfing pins carried by the scarfing roll.

The impact speed is at least about 530 centimeters per second. Preferably the impact speed is at least about 600 centimeters per second, and more preferably is at least about 670 centimeters per second to provide desired benefits. In other aspects of the invention, the impact speed between fibrous web 22 and the scarfing pins is not more than about 3500 centimeters per second. Alternatively, the impact speed is not more than about 3400 centimeters per second, and optionally is not more than about 3300 centimeters per second.

In the illustrated location at which web 22 contacts the scarfing pins on scarfing roll 32, the movement direction of web 22 runs generally opposite and counter to the movement direction of scarfing pins 70. Accordingly, the impact speed between the fibrous material and the scarfing pins is the sum of the web speed and the peripheral surface speed of the scarfing roll.

In an optional configuration of the invention, the movement direction of web 22 can be arranged to run in substantially the same direction as the movement direction of scarfing pins 70. As a result, the relative impact speed between the fibrous web and the scarfing pins would be the difference between the speed of web 22 and the translational speed of the scarfing pins.

It is contemplated that the invention may be constructed and arranged to have conveyor 28 move web 22 at a non-constant, selectively sequenced, variable speed, and to have scarfing roll 32 turn with a non-constant, selectively sequenced, variable rotational velocity. The speed of web 22 and the pin tip velocity on scarfing-roll 32 can be continually adjusted to provide for different impact speeds and/or different scarfing dwell times at predetermined locations along the length dimension of web 22.

Scarfing roll 32 is operatively geared to rotate in coordination with conveyor 28. For example, scarfing roll 32 can be driven off the main machine line shaft and can be timed or registered to cut into web 22 at the desired locations by means of a mechanical, phase shifting differential transmission. A suitable device can, for example, be a Fairchild Specon Model 2:1 PSD transmission, which is available from Fairchild Industrial Products Company, a business having offices in Winston-Salem, N.C.

With reference to FIG. 5, a contoured web 112 formed with the present invention can include opposed, side edge sections 114, medial section 116 and a length dimension 26 which extends along machine direction 30 of the method and apparatus. Contoured web 112 also defines a cross direction 120 and a thickness dimension 118. Distributed along the length dimension 26 of web 112 is a series of low thickness, low basis weight regions 122 and relatively high thickness, high basis weight regions 124. Juxtaposed between the high and low basis regions are transition regions 126 which include a gradually changing basis weight distribution therein. The transition regions 126 are positioned along length dimension 26 and interconnect the low basis weight and high basis weight regions.

Figure 6:
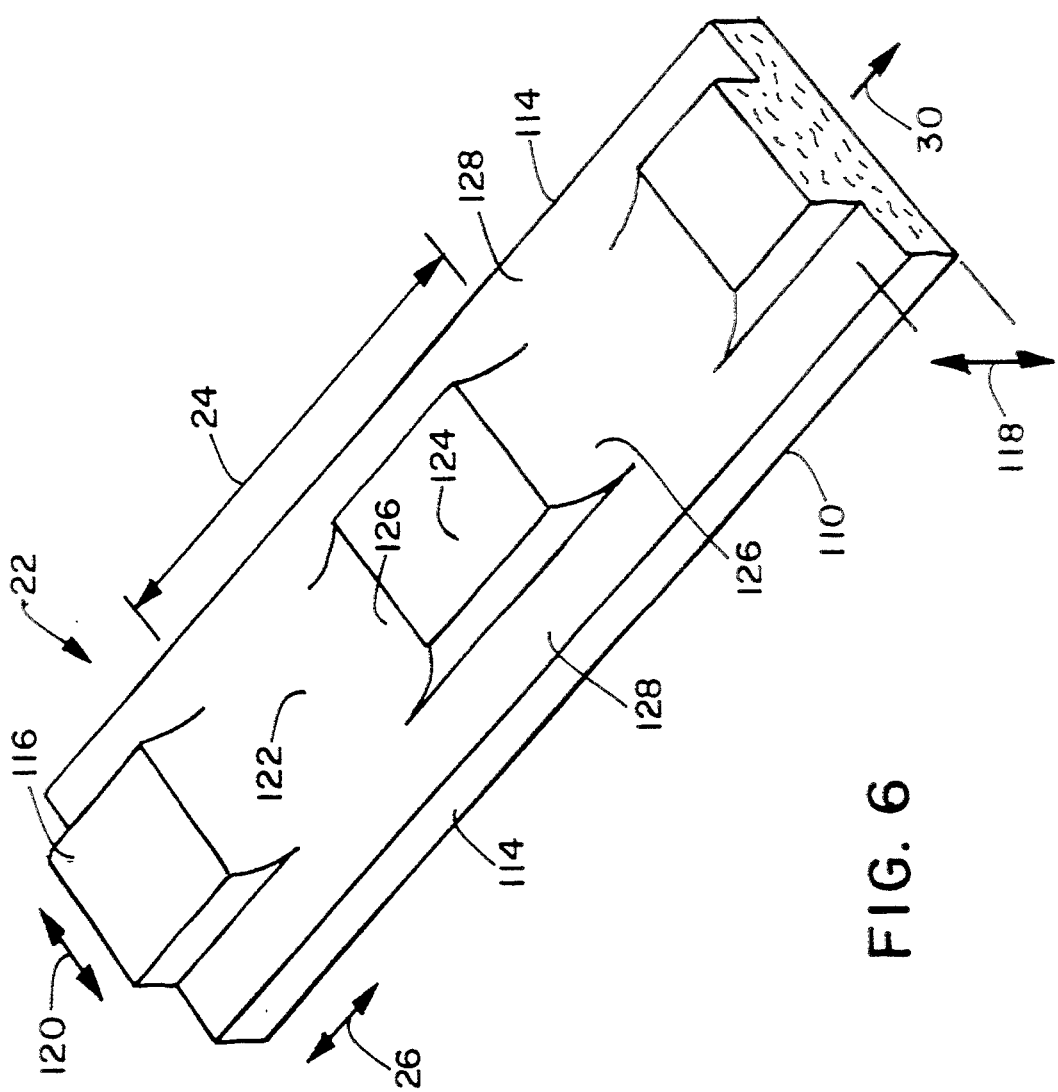
FIG. 6 shows a representative fibrous web which has thickness contours along both the length direction and cross direction of the web.

Fibrous web 22 can also be contoured along its cross direction 120, as representatively shown in FIG. 6. In the shown embodiment, side sections of contoured web 110 can be configured to include relatively low basis weight sections 128. To generate the low basis weight side edge sections, a particular aspect of the invention can have a scarfing means which includes a supplemental scarfing roll 136.

Figure 7A:
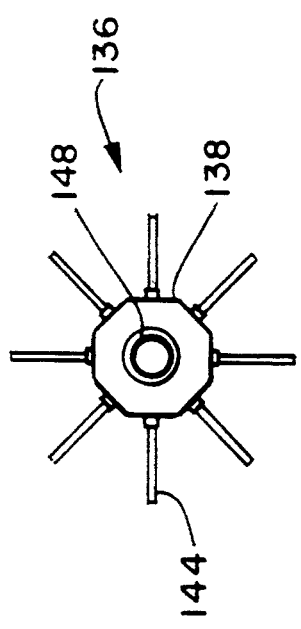
FIG. 7A representatively shows an end view of the supplemental scarfing roll of FIG. 7.
Figure 7:
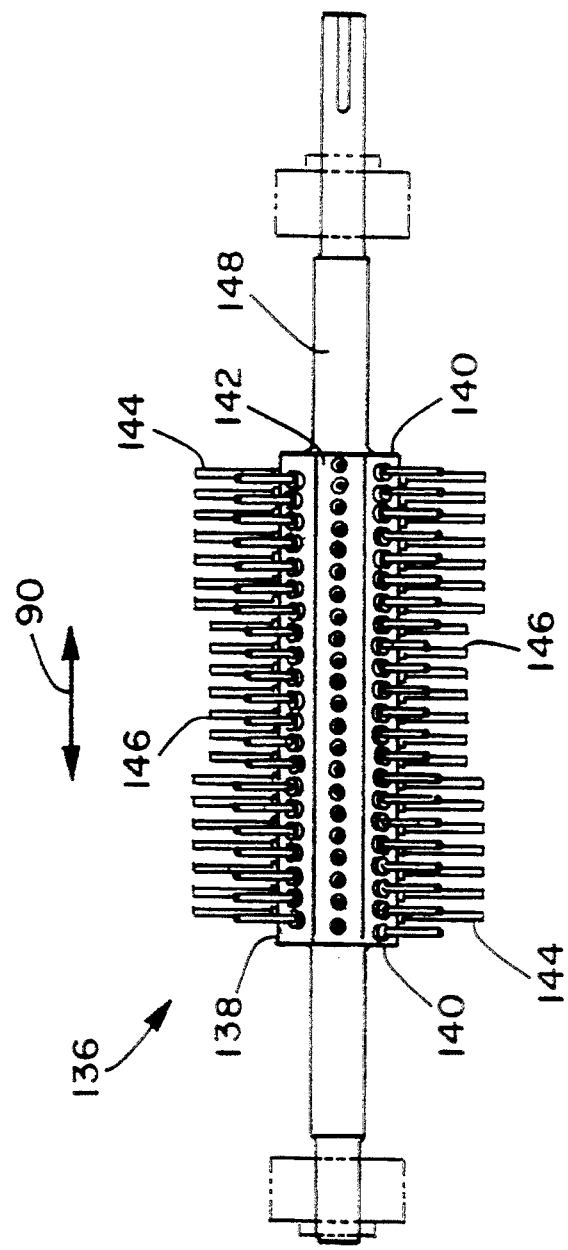
FIG. 7 representatively shows a supplemental scarfing roll for producing a thickness profile along the cross direction of a fibrous web.

As shown in FIGS. 7 and 7A, a representative embodiment of supplemental scarfing roll 136 includes an outer peripheral surface 138 and a rotational axis 148. Outer surface 138 defines side edge sections 140 and medial section 142. The shown embodiment of scarfing roll 136 is configured to generate relatively low basis weight side edge sections. Accordingly, long scarfing pins 144 are located along the side edge sections 140 and relatively short pins 146 are located along medial section 142. In an alternative configuration, scarfing roll 136 may be constructed to produce a contoured web 110 wherein the side edge regions 114 have a relatively higher basis weight than medial section 116. To provide for this distribution of basis weights along the web cross direction 120, scarfing roll 136 may be constructed to have long scarfing pins 114 located along medial section 142 and relatively short pins 146 located along side edge sections 140 of the scarfing roll surface.

It should be appreciated that supplemental scarfing roll 136 need not be timed or specially coordinated with the movement speed of conveyor 28. Scarfing roll 136 should, however, be turned with sufficient rotational speed and velocity to operably remove fibers from fibrous web 22.

Figure 8:
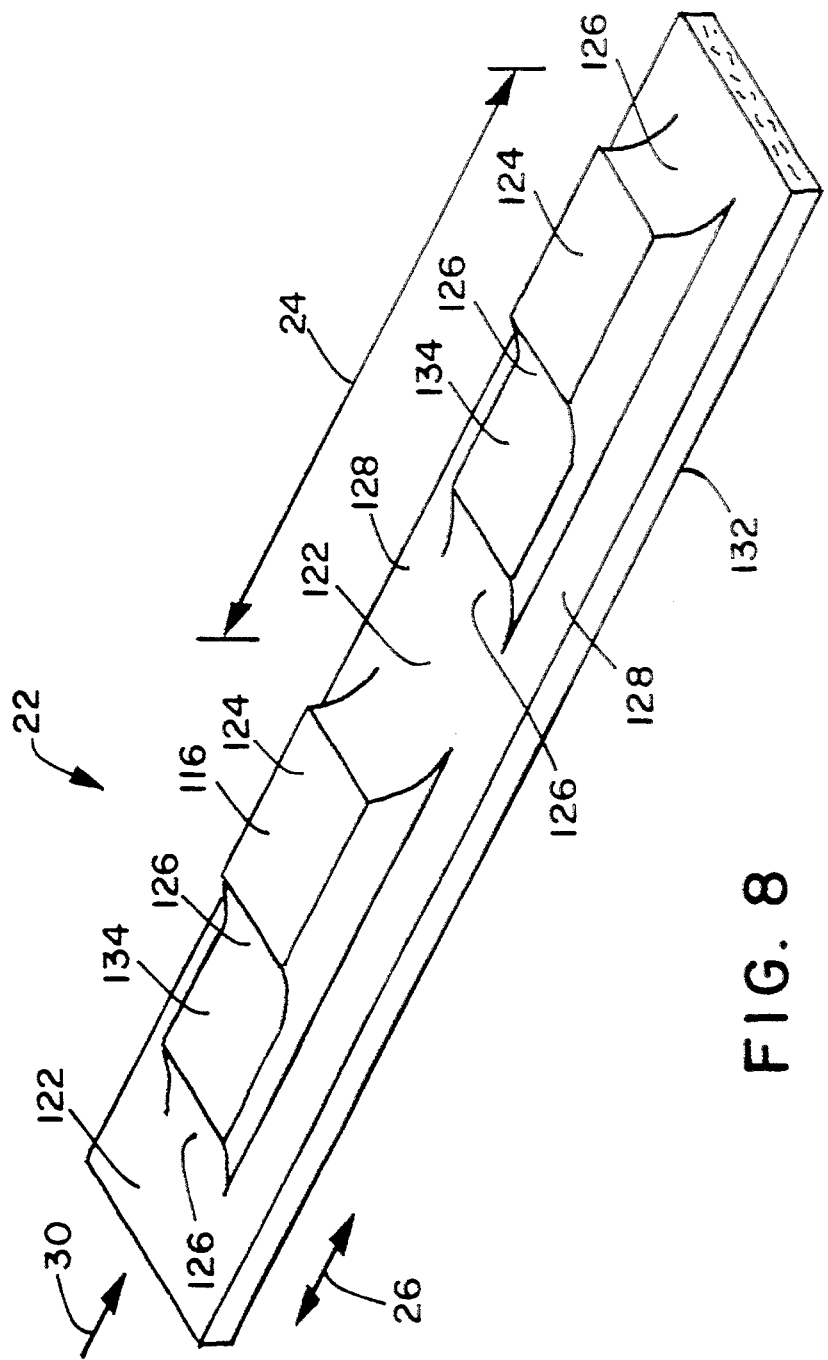
FIG. 8 shows a representative fibrous web having a thickness contour along the cross-direction of the web, and a multiple-step thickness contour along the length direction of the web.

In another aspect of the invention, a multi-step scarfing roll may be employed to produce a multicontoured web 132. As representatively shown in FIG. 8, web 132 has a multi-step variation of fluff basis weight and/or thickness along the length dimension 26 of the fibrous web. Each article segment 24 can, for example, have the predetermined, multi-step thickness variation. In the shown embodiment, each article segment 24 of web 132 has low basis weight side edge sections 128 and a relatively higher basis weight medial section 116. The medial section of web 132 has a low basis weight midportion 122, a relatively high basis weight midportion 124, and a medium basis weight midportion 134. The medium basis weight midportion can, for example, be located between low basis weight midportion 122 and high basis weight midportion 124, and interconnected thereto with transition zones 126.

Figure 9:
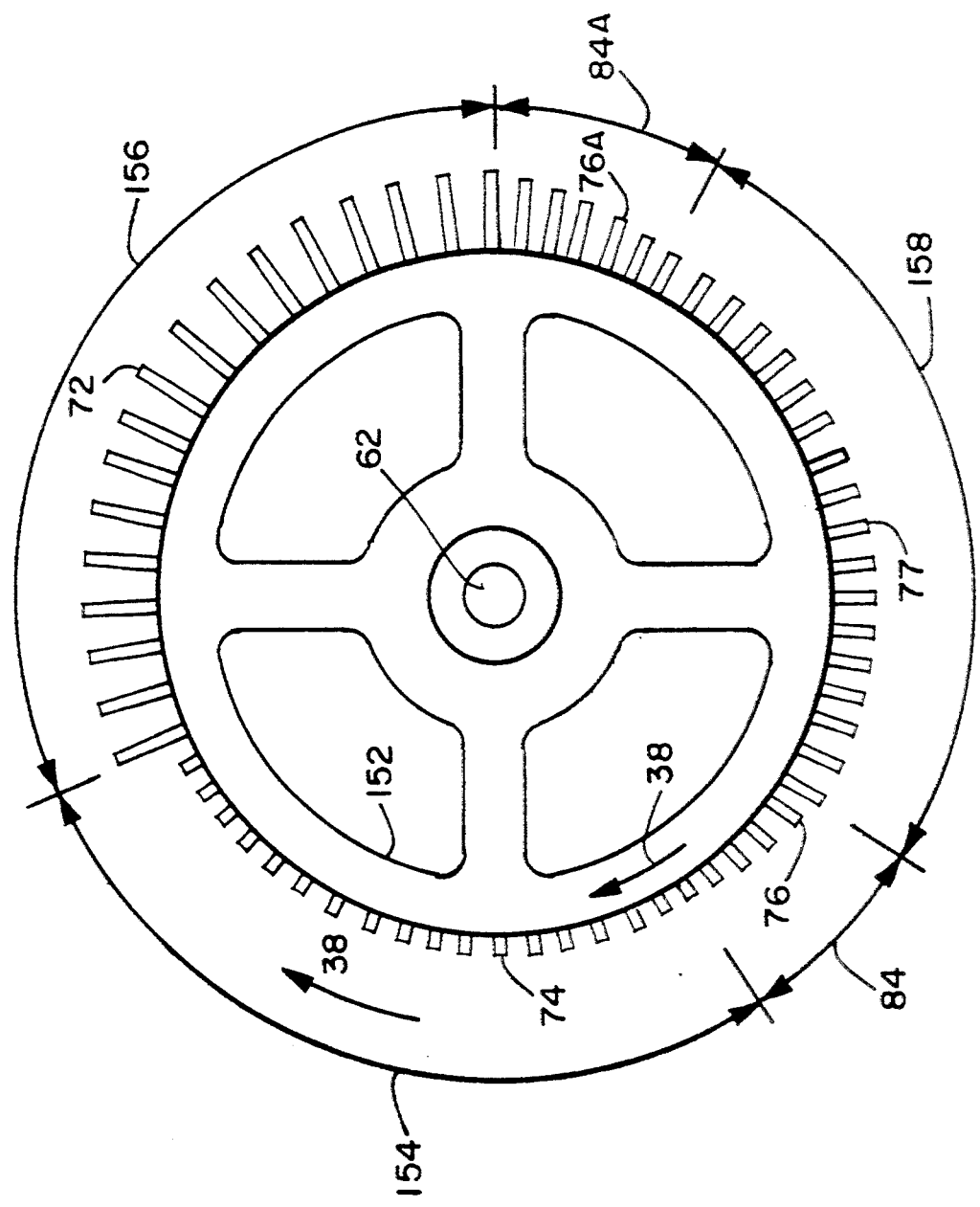
FIG. 9 shows a representative multi-step scarfing roll for producing a multiple-step thickness contour along the length direction of the fibrous web.

With reference to FIG. 9, a timed, multi-step scarfing roll 152 includes an appointed high basis weight section 154, an appointed low basis weight section 156, and an appointed medium basis weight section 158. Short scarfing pins 74 are located in high basis weight section 154, long scarfing pins 72 are located in low basis weight section 156, and medium length scarfing pins 77 are located at medium basis weight section 158. Graduated, intermediate length pins 76 are located at transition sections of scarfing roll 152.

It should be readily apparent that a supplemental scarfing roll 136 may be employed in combination with multi-step roll 152. Such a combination could be employed to produce multi-contoured web 132.

In yet another aspect of the invention, the functions and structures of the timed scarfing roll, such as roll 32 or roll 152, and the supplemental scarfing roll 136 may be combined into a single scarfing roll. Such a combination scarfing roll can advantageously form both length dimensional and cross directional basis weight and/or thickness contours across the surface of web 110 in a substantially simultaneous operation.

Having thus described the invention in rather full detail, it will be readily apparent that various changes and modifications may be made without departing from the spirit of the invention. All of such changes and modifications are contemplated as being within the scope of the present invention, as defined by the subjoined claims.

We claim:

1. A method for contouring a fibrous web, comprising the steps of:
   (a) providing a fibrous web which defines an interconnected series of appointed article segments along a length dimension of said web;
   (b) conveying said web at a selected speed along an appointed machine direction;
   (c) removing and separating away predetermined quantities of fibers from selected regions of said fibrous web with a moving, outer peripheral scarfing surface, said peripheral scarfing surface movable along a selected movement direction thereof, said scarfing surface constructed to provide each of said article segments with a selected contoured basis weight which varies along the length dimension of said segment in a selected correspondence with a predetermined scarfing pattern which is provided by said outer peripheral scarfing surface and is variably patterned along said movement direction of said scarfing surface; and (d) regulating a relative movement between said conveying step (b) to said removing step (c) to provide said selected correspondence and to thereby form said selected contoured basis weight on substantially each of said appointed article segments.

2. A method as recited in claim 1, wherein said removing step comprises the steps of:

rotating a substantially cylindrical scarfing roll having an axis of rotation, and having an outer peripheral surface which extends across a length dimension and a circumferential dimension of said roll;

distributing a plurality of scarfing pins across said outer surface, said pins having lengths thereof arranged to extend at least partially along a radial dimension of said roll, said pins constructed with a plurality of lengths and selectively located to provide for said scarfing pattern.

3. A method as recited in claim 2, further comprising the step of selectively locating said pins to place pins with relatively longer lengths at first regions of said outer surface which are appointed to correspond to relatively low basis weight regions of said article segments, and to place pins with relatively shorter lengths at second regions of said outer surface which are appointed to correspond to relatively high basis weight regions of said article segments.

4. A method as recited in claim 3, further comprising the step of providing said outer surface with at least one transition region which extends along said circumferential dimension, said transition region having a distribution of pins in which the lengths of individual pins are selected to provide a gradual change of pin lengths along said circumferential dimension through said transition region.

5. A method as recited in claim 4, further comprising the step of gradually changing said pin lengths through said transition zone in incremental length changes of not more than about 0.09 cm per degree of circumferential arc length.

6. A method as recited in claim 5, further comprising the step of gradually changing said pin lengths through said transition zone occurs in incremental length changes of not less than about 0.009 cm per degree of circumferential arc length.

7. A method as recited in claim 2, wherein said rotating step rotates said scarfing roll at a rotational velocity which cooperates with said conveying step to provide an impact speed between said moving fibrous web and said scarfing pins of at least about 530 cm/sec.

8. A method as recited in claim 5, wherein said scarfing roll is rotated at a rotational velocity which cooperates with said conveying means to provide an impact speed between said moving fibrous web and said scarfing pins of not more than about 3,500 cm/sec.

9. A method as recited in claim 2, wherein said scarfing pattern is a periodically repeating pattern which repeats a whole-integer number of times along said circumferential dimension of said scarfing roll.

10. A method as recited in claim 7, wherein said whole-integer number substantially corresponds to a number of article segments appointed for movement past said scarfing roll per each revolution of said scarfing roll.

11. A method as recited in claim 1, wherein said scarfing surface further comprises contouring means for providing said article segments with a contoured basis weight which varies along a cross-direction of said web.

12. A method as recited in claim 11, wherein said contouring means comprises a supplemental scarfing roll.

13. A method as recited in claim 11, wherein said contouring means comprises a further scarfing pattern provided by said outer peripheral scarfing surface, and said pattern is configured to have a variation along a cross-direction of said scarfing surface.

14. A method as recited in claim 11, wherein said scarfing surface is further constructed to provide each of said article segments with a contoured, multi-step basis weight variation along the length dimension of said web in a selected correspondence with a multi-step scarfing pattern provided by said outer peripheral scarfing surface, said scarfing pattern having a multi-step variation along said movement direction of said scarfing means.

15. A method as recited in claim 14, wherein said multi-step scarfing pattern is further configured to have a variation along a cross-direction of said scarfing means.

16. A method as recited in claim 15, wherein said scarfing surface is provided by an outer peripheral surface of a scarfing roll, and said multi-step scarfing pattern is a periodically repeating pattern which repeats a whole-integer number of times along a circumferential dimension of said scarfing roll, and said whole-integer number substantially corresponds to a number of article segments appointed for movement past said scarfing roll per each revolution thereof.

17. A method as recited in claim 5, wherein said gradual change of pin lengths through said transition zone occurs in incremental length changes of not more than about 0.05 cm per degree of circumferential arc length.

18. A method as recited in claim 5, wherein said gradual change of pin lengths through said transition zone occurs in incremental length changes of not more than about 0.03 cm per degree of circumferential arc length.

19. A method as recited in claim 6, wherein said gradual change of pin lengths through said transition zone occurs in incremental length changes of not less than about 0.012 cm per degree of circumferential arc length.

20. A method as recited in claim 6, wherein said gradual change of pin lengths through said transition zone occurs in incremental length changes of not less than about 0.02 cm per degree of circumferential arc length.

* * * * *